(12) United States Patent
Sulzer et al.

(10) Patent No.: US 10,682,077 B2
(45) Date of Patent: Jun. 16, 2020

(54) MECHANICAL AUDIO AND HAPTIC FEEDBACK DEFLECTION BEAM

(71) Applicants: BOARD OF REGENTS, THE UNIVERSITY OF TEXAS SYSTEM, Austin, TX (US); SETON HEALTHCARE FAMILY, Austin, TX (US)

(72) Inventors: James S. Sulzer, Austin, TX (US); Jose J. Mendez, Jr., Austin, TX (US); Nicholas D. Phillips, Austin, TX (US); Lisa Stevens, Austin, TX (US); Curtis Merring, Austin, TX (US)

(73) Assignees: BOARD OF REGENTS, THE UNIVERSITY OF TEXAS SYSTEM, Austin, TX (US); SETON HEALTHCARE FAMILY, Austin, TX (US)

( * ) Notice: Subject to any disclaimer, the term of this patent is extended or adjusted under 35 U.S.C. 154(b) by 240 days.

(21) Appl. No.: 15/568,109

(22) PCT Filed: Apr. 22, 2016

(86) PCT No.: PCT/US2016/028749
§ 371 (c)(1),
(2) Date: Oct. 20, 2017

(87) PCT Pub. No.: WO2016/172416
PCT Pub. Date: Oct. 27, 2016

(65) Prior Publication Data
US 2018/0085033 A1    Mar. 29, 2018

Related U.S. Application Data

(60) Provisional application No. 62/150,957, filed on Apr. 22, 2015.

(51) Int. Cl.
*A61B 5/11*     (2006.01)
*A61B 5/00*     (2006.01)
*G08B 6/00*     (2006.01)

(52) U.S. Cl.
CPC .......... *A61B 5/1126* (2013.01); *A61B 5/1121* (2013.01); *A61B 5/4566* (2013.01);
(Continued)

(58) Field of Classification Search
CPC .......... A61B 5/11–1135; A61B 5/6833; A61B 2562/0261; A61B 5/1071; A61B 5/4528;
(Continued)

(56) References Cited

U.S. PATENT DOCUMENTS 2,064,603 A    12/1936  Harrison
2,809,042 A    10/1957  Wasley
(Continued)

FOREIGN PATENT DOCUMENTS

CN     103308024          2/2016
DE     202015006659 U1 *  12/2015    ........... A61B 5/1116
(Continued)

OTHER PUBLICATIONS

International Search Report and Written Opinion issued in International Application No. PCT/US2016/028749, dated Jul. 15, 2016.

*Primary Examiner* — Catherine B Kuhlman
(74) *Attorney, Agent, or Firm* — Parker Highlander PLLC

(57) ABSTRACT

Devices and methods for detecting joint motion of a user. In particular embodiments, devices may comprise a deflectable beam coupled to a user via adhesive pads located between the neck and shoulder of the use. Audio and haptic feedback can be provided to the user when the deflectable beam deflects due to motion of the joint.

17 Claims, 3 Drawing Sheets

(52) U.S. Cl.
CPC .......... *A61B 5/4576* (2013.01); *A61B 5/6814* (2013.01); *A61B 5/6822* (2013.01); *A61B 5/6833* (2013.01); *A61B 5/7405* (2013.01); *A61B 5/7455* (2013.01); *G08B 6/00* (2013.01); *A61B 5/4528* (2013.01)

(58) Field of Classification Search
CPC ....... A61B 5/4538–4595; A61B 5/6813–6829; A61B 5/74–7495; G01L 1/22–2293; G01B 5/30; G01B 7/16
See application file for complete search history.

(56) References Cited

U.S. PATENT DOCUMENTS

| | | | |
|---|---|---|---|
| 3,350,100 A | 10/1967 | Carmines | |
| 4,222,569 A | 9/1980 | DeMascolo | |
| 4,414,537 A * | 11/1983 | Grimes | A61B 5/1114 341/20 |
| 4,444,205 A | 4/1984 | Jackson | |
| 4,800,897 A | 1/1989 | Nilsson | |
| 4,895,372 A | 1/1990 | Muller | |
| 4,897,927 A * | 2/1990 | Nicol | A61B 5/1071 33/512 |
| 5,086,785 A * | 2/1992 | Gentile | A61B 5/1126 338/210 |
| 5,146,929 A | 9/1992 | Sawhill | |
| 5,522,401 A | 6/1996 | Brucker | |
| 5,743,806 A | 4/1998 | Brennan | |
| 5,876,292 A | 3/1999 | Hamilton | |
| 6,032,530 A | 3/2000 | Hock | |
| 6,119,516 A | 9/2000 | Hock | |
| 6,447,425 B1 | 9/2002 | Keller et al. | |
| 7,980,141 B2 | 7/2011 | Connor et al. | |
| 2003/0083596 A1 | 5/2003 | Kramer et al. | |
| 2009/0324161 A1 * | 12/2009 | Prisco | G01L 1/246 385/13 |
| 2010/0036287 A1 * | 2/2010 | Weber | A61B 5/1116 600/595 |
| 2010/0234182 A1 * | 9/2010 | Hoffman | A61B 5/1125 482/8 |
| 2010/0286950 A1 * | 11/2010 | Heijkants | A61B 5/1071 702/151 |
| 2011/0006902 A1 * | 1/2011 | Saigh | A61B 5/1126 340/573.1 |
| 2011/0202306 A1 | 8/2011 | Eng et al. | |
| 2013/0198625 A1 | 8/2013 | Anderson et al. | |
| 2014/0070957 A1 | 3/2014 | Longinotti-Buitoni et al. | |
| 2014/0128689 A1 | 5/2014 | Stewart et al. | |
| 2015/0257654 A1 * | 9/2015 | Bennett-Guerrero | A61B 5/1121 600/301 |
| 2017/0014049 A1 * | 1/2017 | Dumanyan | A61B 5/7203 |

FOREIGN PATENT DOCUMENTS

| | | | | |
|---|---|---|---|---|
| WO | WO-0137730 A1 * | 5/2001 | ............ | A61B 5/103 |
| WO | WO 2005/018453 | 3/2005 | | |

* cited by examiner

MECHANICAL AUDIO AND HAPTIC FEEDBACK DEFLECTION BEAM

CROSS-REFERENCE TO RELATED APPLICATIONS

This applications is a national application under 35 U.S.C. § 371 of International Application No. PCT/US2016/028749 filed on Apr. 22, 2016, which claims priority to U.S. Provisional Patent Application Ser. No. 62/150,957 filed Apr. 22, 2015, the entire contents of each of which are incorporated herein by reference.

BACKGROUND INFORMATION

Existing methods for monitoring joint movement include shortcomings that have not been adequately addressed. For example, currently the traditional method in therapy for "shoulder hiking" is to undergo a set of exercises in front of a mirror or with the guidance of a clinician or assistant. This traditional method requires many hours of observation of the patient for corrections that could be used for other purposes. This method also does not allow the patient to work independently to improve their condition for better results.

There is presently a shortage of devices and methods that provide independence to the patient. Exemplary embodiments of the device and methods disclosed herein promote patient independence by providing audio and haptic feedback of excessive shoulder hiking to the user. Exemplary embodiments not only meet the desired criteria, but can also be applied for other uses around joints, the torso, or neck.

SUMMARY

Exemplary embodiments of the present disclosure address the issues described above. As explained more fully below, in one exemplary embodiment the device comprises a deflectable beam configured to provide audio and haptic feedback to the user when the deflectable beam is deflected due to joint movement. In specific embodiments the deflectable beam comprises a first end and a second end, and the device comprises a first support coupled to the deflectable beam proximal to the first end and a second support coupled to the deflectable beam proximal to the second end. In particular embodiments, the device also includes a first adhesive pad coupled to the first support; and a second adhesive pad coupled to the second support. Exemplary embodiments also include method of using devices as described herein.

Exemplary embodiments of the present disclosure provide numerous benefits over existing technologies. For example, exemplary embodiments are mechanical in nature and do not require expensive or complicated electronics for operation. In addition, exemplary embodiments provide audio and haptic feedback upon deflection. Dimensions of the deflectable beam can be altered for different applications (e.g. to monitor different joints).

Exemplary embodiments are also user friendly, inexpensive to produce, and can be easily attached and removed from the user. Such benefits allow for independent operation by the patient/user, and can promote time efficiency for clinicians and tech assistants. This can allow for a safe and comfortable interaction with the patient.

Embodiments of the devices and methods disclosed herein address the issue of detecting joint movement (e.g. the elevation of the shoulder on the user) while undergoing therapy without needing the constant observation of technicians and promotes independence through each therapy session. Exemplary embodiments use can be expanded to other applications that require detection of excessive joint movement.

Exemplary embodiments are also advantageous by providing purely mechanical feedback, as opposed to other devices and methods that use electronics. Exemplary embodiments are also easy to use and fabricate.

In the present disclosure, the term "coupled" is defined as connected, although not necessarily directly, and not necessarily mechanically.

The use of the word "a" or "an" when used in conjunction with the term "comprising" in the claims and/or the specification may mean "one," but it is also consistent with the meaning of "one or more" or "at least one." The terms "approximately, "about" or "substantially" mean, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method or device that "comprises," "has," "includes" or "contains" one or more steps or elements, possesses those one or more steps or elements, but is not limited to possessing only those one or more elements. Likewise, a step of a method or an element of a device that "comprises," "has," "includes" or "contains" one or more features, possesses those one or more features, but is not limited to possessing only those one or more features. Furthermore, a device or structure that is configured in a certain way is configured in at least that way, but may also be configured in ways that are not listed.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF ILLUSTRATIVE EMBODIMENTS

Figure 1:
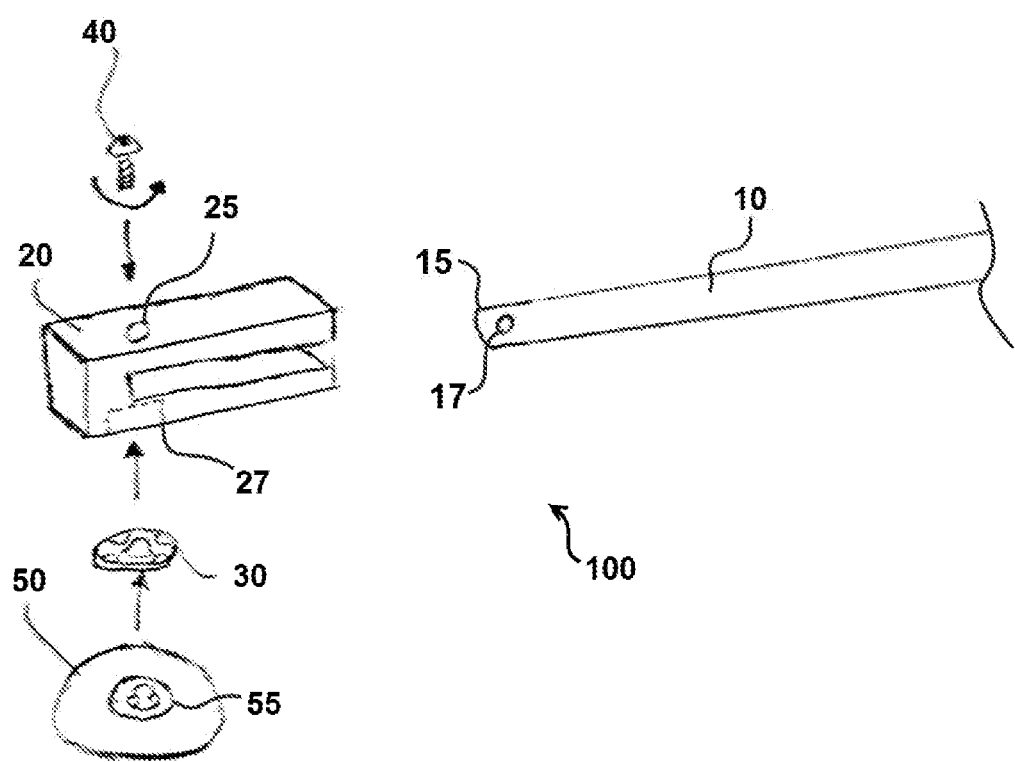
FIG. 1 illustrates an exploded view of one portion an exemplary embodiment of device according to the present disclosure.
Figure 2:
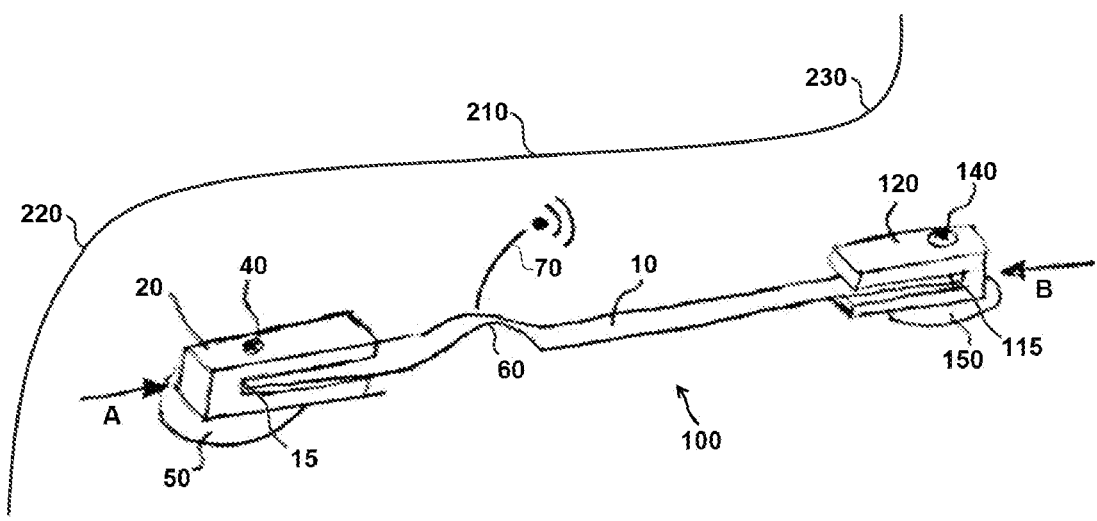
FIG. 2 illustrates a perspective view of the embodiment of FIG. 1 during use.
Figure 3:
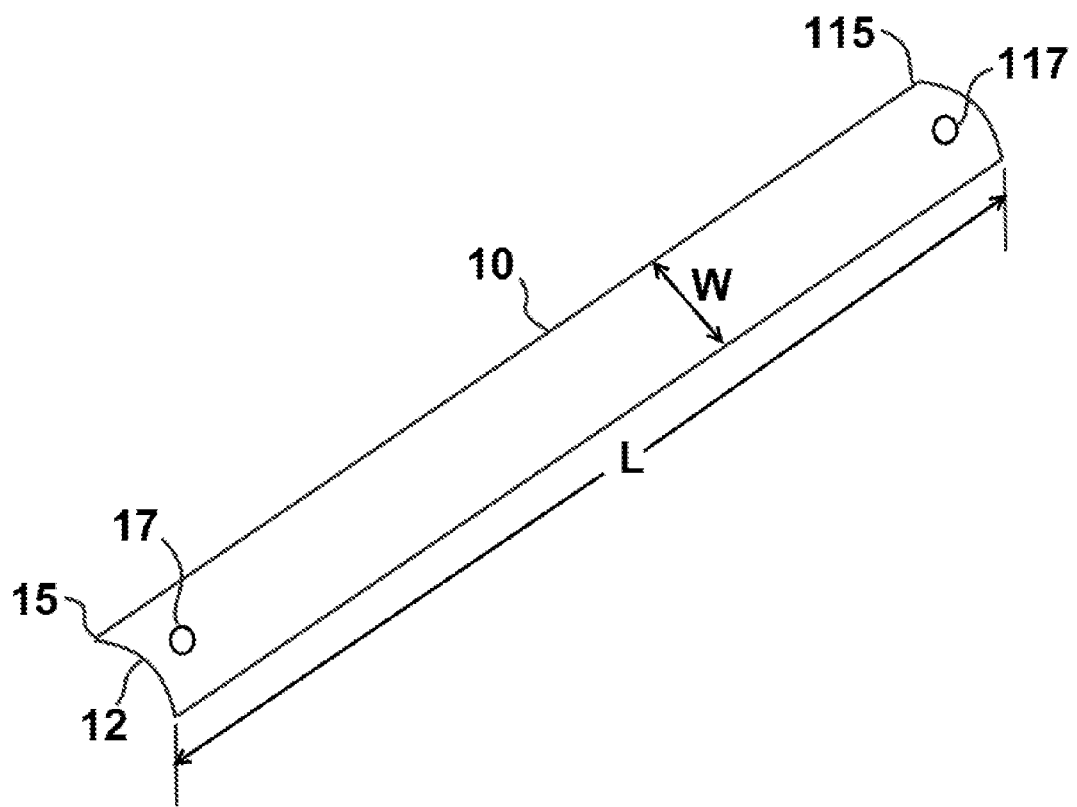
FIG. 3 illustrates a perspective view of a component of the embodiment of FIG. 1.

Referring now to FIGS. 1-3, a device 100 for detecting joint motion of a user is illustrated. FIG. 1 illustrates an exploded view of one half of device 100. It is understood the other half of device 100 not shown in FIG. 1 is equivalent to the portion shown in FIG. 1. FIG. 2 illustrates a perspective view of device 100 during use, while FIG. 3 illustrates a perspective view of a deflectable beam 10 of device 100.

In this embodiment, device 100 comprises deflectable beam 10 comprising a first end 15 and a second end 115. The illustrated embodiment further comprises a first support 20 coupled to deflectable beam 10 proximal to first end 15, and a second support 120 coupled to deflectable beam 10 proximal to second end 115. In specific embodiments first support 20 and second support 120 may be configured as U-shaped brackets such that ends 15 and 115 can be inserted into the brackets. In particular embodiments, first support 20 and second support 120 can be coupled to first and second adhesive pads 50 and 150, respectively. In specific embodiments, first and second adhesive pads 50 and 150 may be components that are also configured for use in electrocardiograms, and in particular, as electrocardiogram electrodes.

Adhesive pads 50 and 150 can be used to couple device 100 to a user 210 (e.g. by adhering to the skin of user 210 in an area proximal to the joint in which it is desired to detect motion). In the embodiment shown in FIG. 2, device 100 has been coupled to user 210 in an area between shoulder 220 and neck 230. In this location, device 100 can detect motion of shoulder 220 to provide audio and haptic feedback to user 210 when shoulder 220 has extended past a particular range of motion.

For example, as shoulder 220 is raised, adhesive pad 50 will move because it is coupled to user 210 in an area proximal to should 220. Adhesive pad 150, which is distal to shoulder 220 (relative to adhesive pad 50), will not move an amount equivalent to that of adhesive pad 50. Accordingly, the distance between adhesive pads 50 and 150 will decrease as shoulder 220 is raised. This decrease in distance between adhesive pads 50 and 150 will lead to a corresponding decrease in the distance between supports 40 and 140, which are coupled to ends 15 and 115 of deflectable beam 10. Accordingly, supports 40 and 140 will exert a compressive force on beam 10 in the direction of arrows A and B. When shoulder 220 is raised a sufficient amount, a deflection 60 will form in deflectable beam 10 and an audio feedback (e.g. an audible noise) 70 will be emitted as a result of the deflection. In addition, deflection 60 will result in a decreased stiffness in deflectable beam. The reduction in stiffness can provide haptic feedback to user 210 in addition to the audio feedback from audible noise 70. This feedback can alert user 210 that shoulder 220 has been raised to a particular threshold in the range of motion.

Referring specifically now to FIG. 1, in certain embodiments, first support 20 can coupled to deflectable beam 10 via a threaded fastener 40 and a snap member 30. It is understood that other embodiments may comprise different coupling mechanisms, including for example combinations of rivets, hook-and-loop fasteners, etc. In the embodiment shown, threaded fastener 40 may be inserted through an orifice 25 in first support 20 and an orifice 17 in deflectable beam. In certain embodiments, threaded fastener 40 can be threaded into first support 20 and/or deflectable beam 10. In some embodiments, threaded fastener 40 may be threaded into snap member 30. Snap member 30 can be inserted into a cavity 27 in first support 20, and snap member 30 can then be coupled to adhesive pad 50 (which also comprises a snap member 55). In this manner, first support 20 can be coupled to deflectable beam 10 and adhesive pad 50. It is understood that the second support 120 can be coupled to deflectable beam 10 and adhesive pad 150 via threaded fastener 140 in an equivalent manner. As shown in FIG. 3, deflectable beam 10 also comprises an orifice 117 proximal to end 115 through which threaded fastener 140 may be inserted.

In the embodiment illustrated in FIG. 3, deflectable beam 10 comprises a length L and width W. In particular embodiments, L may range from two inches to five inches, or more particularly from three inches to four inches, or more particularly approximately 3.5 inches. In certain embodiments, W may range from 0.15 inches to 0.35 inches, or more particularly from 0.2 inches to 0.3 inches, or more particularly approximately 0.25 inches. In particular embodiments, deflectable beam 10 can have a thickness (e.g. the dimension orthogonal to width W and length L) of less than 0.010 inches. In specific embodiments, deflectable beam 10 may have a thickness of less than 0.005 inches.

In the embodiment shown, deflectable beam 10 comprises a curved profile 12 across width W. In some embodiments, deflectable beam 10 is a metal beam, and particular embodiments a steel beam. In certain embodiments, deflectable beam 10 may be formed from crinkle material, including for example, material used in children's toys. The mechanical properties and shape of deflectable beam 10 (including for example, the material, length, width, and the curved profile) can provide for particular audio feedback upon beam deflection. In exemplary embodiments, deflectable beam 10 is excited to its natural frequency which is in the audible range for humans, and the emitted amplitude of the frequency is high enough to be heard by user 210. Accordingly, device 100 can provide audio and haptic feedback when shoulder 220 elevates so as to detect excessive joint range of motion for therapeutic use in a clinic and possibly outside the clinic.

All of the devices, systems and/or methods disclosed and claimed herein can be made and executed without undue experimentation in light of the present disclosure. While the devices, systems and methods of this invention have been described in terms of particular embodiments, it will be apparent to those of skill in the art that variations may be applied to the devices, systems and/or methods in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

The contents of the following references are incorporated by reference herein:
U.S. Pat. No. 2,064,603
U.S. Pat. No. 2,809,042
U.S. Pat. No. 3,350,100
U.S. Pat. No. 4,800,897
U.S. Pat. No. 4,895,372
U.S. Pat. No. 5,146,929
U.S. Pat. No. 5,522,401
U.S. Pat. No. 5,743,806
U.S. Pat. No. 5,876,292
U.S. Pat. No. 6,032,530
U.S. Pat. No. 6,119,516
U.S. Pat. No. 6,447,425
U.S. Pat. No. 7,980,141
U.S. Patent Publication 2014/0128689

The invention claimed is:

1. A device for detecting joint motion of a user, the device comprising:
    a deflectable beam comprising a first end and a second end;
    a first support coupled to the deflectable beam proximal to the first end;

a second support coupled to the deflectable beam proximal to the second end;
a first adhesive pad coupled to the first support; and
a second adhesive pad coupled to the second support, wherein:
the deflectable beam has a length extending between the first end and the second end;
the deflectable beam has a width perpendicular to the length;
the deflectable beam has a curved profile across the width of the deflectable beam;
the deflectable beam is a metal beam;
the deflectable beam is configured to provide audio and haptic feedback to the user when the deflectable beam is deflected; and
the haptic feedback results from a decreased stiffness of the deflectable beam.

2. The device of claim 1 wherein the device is configured to be coupled to a user in an area proximal to a joint.

3. The device of claim 2 wherein the deflectable beam is configured to deflect when the joint is moved by the user.

4. The device of claim 2 wherein the joint is a shoulder joint.

5. The device of claim 2 wherein the joint is a neck joint.

6. The device of claim 1 wherein:
the first adhesive pad is coupled to the first support via a first snap member and a second snap member; and
the second adhesive pad is coupled to the second support via a third snap member and a fourth snap member.

7. The device of claim 6 wherein:
the first snap member is inserted into a first cavity in the first support;
the second snap member is coupled to the first adhesive pad;
the third snap member is inserted into a second cavity in the second support;
and the fourth snap member is coupled to the second adhesive pad.

8. The device of claim 1 wherein the audio feedback is in the audible range for a human.

9. The device of claim 1 wherein the deflectable beam is configured to provide secondary audio feedback when the deflectable beam moves from a deflected position to a straight position.

10. The device of claim 1 wherein the deflectable beam:
the length is between two inches and five inches;
the width is between 0.15 inches and 0.35 inches; and
the deflectable beam has a thickness less than 0.010 inches.

11. A method of detecting movement of a joint of a user, the method comprising:
coupling a device comprising a deflectable beam to an area proximal to the joint; and
moving the joint an amount sufficient to cause a deflection of the deflectable beam,
wherein:
the deflectable beam has a length extending between the first end and the second end;
the deflectable beam has a width perpendicular to the length;
the deflectable beam has a curved profile across the width of the deflectable beam;
the deflectable beam is a metal beam;
the deflection of the deflectable beam produces an audio and haptic feedback to the user; and
the haptic feedback results from a decreased stiffness of the deflectable beam.

12. The method of claim 11 wherein coupling the device comprising the deflectable beam to the area proximal to the joint comprises coupling adhesive pads to the user.

13. The method of claim 11 wherein the joint is a shoulder joint.

14. The method of claim 11 wherein the joint is a neck joint.

15. The method of claim 11 wherein the audio feedback is in the audible range for a human.

16. The method of claim 11 wherein the deflectable beam is configured to provide secondary audio feedback when the deflectable beam moves from a deflected position to a straight position.

17. The method of claim 14 wherein the deflectable beam:
has a length between two inches and five inches;
has a width between 0.15 inches and 0.35 inches; and
has a thickness less than 0.010 inches.

* * * * *